(12) United States Patent
Yoshitomo

(10) Patent No.: US 7,875,743 B2
(45) Date of Patent: Jan. 25, 2011

(54) BIS(FORMYLPHENYL)ALKANE AND NOVEL POLYNUCLEAR PHENOL DERIVED FROM THE SAME

(75) Inventor: Akira Yoshitomo, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 112 days.

(21) Appl. No.: 12/445,259

(22) PCT Filed: Oct. 3, 2007

(86) PCT No.: PCT/JP2007/069353

§ 371 (c)(1),
(2), (4) Date: May 12, 2009

(87) PCT Pub. No.: WO2008/044568

PCT Pub. Date: Apr. 17, 2008

(65) Prior Publication Data

US 2010/0016633 A1    Jan. 21, 2010

(30) Foreign Application Priority Data

Oct. 13, 2006    (JP) .............................. 2006-280209

(51) Int. Cl.
*C07C 59/40* (2006.01)
(52) U.S. Cl. ..................................... 562/468
(58) Field of Classification Search ................ 562/468
See application file for complete search history.

(56) References Cited

U.S. PATENT DOCUMENTS 5,218,077 A * 6/1993 St. Clair et al. ............. 528/188
5,599,974 A   2/1997 Abraham et al.

FOREIGN PATENT DOCUMENTS

| JP | 05-125032   | 5/1993  |
|----|-------------|---------|
| JP | 05-301453   | 11/1993 |
| JP | 11-199533   | 7/1999  |
| JP | 2000-001448 | 1/2000  |
| JP | 2000-333601 | 12/2000 |
| JP | 2004-290100 | 10/2004 |
| JP | 2004-313177 | 11/2004 |
| JP | 2006-078744 | 3/2006  |

OTHER PUBLICATIONS

Maeng, Ki Suck, et al., "Methylene-bis-salicylaldehyde," Reports Res. Inst. Ind. Tech. Dev., Chungnam Nat. Univ., vol. 4, No. 2, Dec. 1977.

* cited by examiner

*Primary Examiner*—Daniel M Sullivan
*Assistant Examiner*—Jennifer C Sawyer
(74) *Attorney, Agent, or Firm*—Knobbe Martens Olson & Bear LLP

(57) ABSTRACT

Manufacture a novel bis(formylphenyl)alkane according to General Formula (1), as well as a novel polynuclear phenol derived therefrom, by causing a bis(hydroxymethyl-hydroxyphenyl)alkane to react with hexamethylene tetramine in the presence of an acid and hydrolyzing the reaction product, and then using the obtained bis(hydroxy-formylphenyl)alkane as a direct material and causing this material to react with halogenated alkoxycarbonyl hydrocarbon in the presence of a base.

5 Claims, No Drawings

BIS(FORMYLPHENYL)ALKANE AND NOVEL POLYNUCLEAR PHENOL DERIVED FROM THE SAME

This application is the U.S. National Phase under 35 U.S.C. §371 of International Application PCT/JP2007/069353, filed on Oct. 3, 2007, which claims priority to Japanese Patent Application No. 2006-280209, filed on Oct. 13, 2006. The International Application was published under PCT Article 21(2) in a language other than English.

TECHNICAL FIELD

The present invention relates to a novel bis(formylphenyl)alkane, as well as a novel polynuclear phenol derived therefrom, and more specifically to a novel bis(formylphenyl)alkane having, on each phenyl nucleus, a formyl group and an ether group being a nucleus substitution group, as well as a polynuclear phenol constituted by such bis(formylphenyl)alkane whose formyl groups are each substituted by two phenol groups.

PRIOR ART

Traditionally some chemical compounds are known that are classified as "bis(formylphenyl)." For example, a bis(formylphenol) obtained from salicylaldehyde and formaldehyde is described in Chungnam National University Industrial Technology Lab Papers, Vol. 4, No. 2 (1977).

Also, a tetraformylated bisphenol is described in Japanese Patent Laid-open No. Hei 5-125032. In addition, a compound obtained by substituting the hydroxyl groups of a bis(formylphenol) with t-butoxycarbonylmethoxy is described in the European Journal of Organic Chemistry, 2000, 1923-1931, while a bisbenzaldehyde having aromatic carboxyl groups and bonded with ether or ester groups is described in U.S. Pat. No. 5,599,974.

However, despite the demand in recent years for bis(formylphenyl) offering more versatile performance for use in various industrial fields, such as use as a material for photoresist, etc., no bis(formylphenyl)alkane has been known that has, on each phenyl nucleus, as nucleus substitution groups, a formyl group as well as an ether group bonded by a carboxy substituted aromatic hydrocarbon group or alkoxycarbonyl substituted aromatic hydrocarbon group.

In the mean time, such bis(formylphenyl)alkane compounds having, as nucleus substitution groups, a formyl group as well as an ether group bonded by a carboxy substituted aromatic hydrocarbon group or alkoxy carbonyl substituted aromatic hydrocarbon group, would offer excellent heat resistance, represented by high glass transfer temperature, etc., and also presents excellent reactivity with phenols due to its formyl group, as well as excellent reactivity due to the ester group or carboxyl group at the end. Accordingly, such bis(formylphenyl)alkane compounds would be useful as a modifier for phenol resins, etc., photoresist material, intermediate material for various polynuclear phenol compounds obtained through reaction with phenols, etc., or reactive intermediate material, etc., for making polynuclear aromatic compounds, etc., that offer excellent heat resistance, among others.

On the other hand, various polynuclear phenol compounds are known, including a compound constituted by a bis(hydroxyphenyl) where four hydroxyphenyl groups are bonded to a phenyl group via a methylene group, as disclosed in Japanese Patent Laid-open Nos. Hei 11-1 99533 and 2000-1448. However, polynuclear phenol compounds offering even higher glass transition temperatures or more versatile performance are currently in need.

Polynuclear phenol compounds obtained from a novel bis(formylphenyl)alkane according to the present invention are expected to offer excellent heat resistance, but no such polynuclear phenol compounds have been known to date. In the meantime, such polynuclear phenol compounds would be useful as materials for photosensitive resist compositions such as EUV, materials and hardeners for epoxy resins, color development agents and anti-fade agents used in thermosensitive recording materials, bactericides, fungicides, antioxidants, and so on.

Patent Literature 1: Japanese Patent Laid-open No. Hei 5-125032

Patent Literature 2: U.S. Pat. No. 5,599,974

Patent Literature 3: Japanese Patent Laid-open No. Hei 11-199533

Patent Literature 4: Japanese Patent Laid-open No. 2000-1448

Non-patent Literature 5: Chungnam National University Industrial Technology Lab Papers, Vol. 4, No. 2 (1977)

SUMMARY OF THE INVENTION

Problems to Be Solved By the Invention

The present invention was developed in light of the aforementioned condition involving conventional bis(formylphenyl), and it is an object of the present invention to provide a novel bis(formylphenyl)alkane having, on each phenyl nucleus, as nucleus substitution groups, a formyl group as well as an ether group bonded by a carboxy substituted aromatic hydrocarbon group or alkoxy carbonyl substituted aromatic hydrocarbon group, and to provide a polynuclear phenol constituted by the above bis(formylphenyl)alkane whose formyl groups are each substituted further by two hydroxyphenyl groups.

Means for Solving the Problems

A novel bis(formylphenyl)alkane conforming to the present invention is expressed by General Formula (1) below:

[Chemical 1]

General Formula (1)

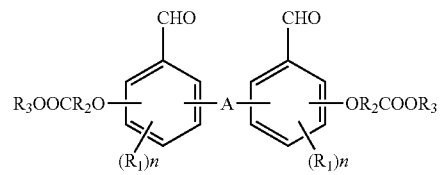

(wherein A represents a saturated aliphatic hydrocarbon group with 1 to 9 carbon atoms, each $R_1$ independently represents a hydrocarbon, alkyl group with 1 to 8 carbon atoms or alkoxy group with 1 to 8 carbon atoms, n represents an integer of 0 to 3, $R_2$ represents a single-ring or condensed-ring aromatic hydrocarbon group with 6 to 15 carbon atoms that may have an aliphatic hydrocarbon group with 1 to 8 carbon atoms in its main chain, and $R_3$ represents a hydrogen atom or alkyl group with 1 to 6 carbon atoms)

In General Formula (1) above, specific examples of the saturated aliphatic hydrocarbon group with 1 to 9 carbon atoms, represented by A, include a methylene group, 2,2-propylidene group, 1,1-propylidene group, 2-methyl-4,4-pentylidene group, 2,2-butylidene group or other straight-chain, branched-chain or cyclic alkylidene group having phenyl groups bonded to the same carbon atom, as well as an ethylene group, propylene group, pentamethylene group, hexamethylene group or other straight-chain, branched-chain or cyclic alkylene group not having phenyl groups bonded to the same carbon atom. If A is an alkylidene group expressed by General Formula (5) below, $R_{11}$ and $R_{12}$ should preferably be a hydrogen atom or primary or secondary alkyl group, or more preferably a hydrogen atom or alkyl group with 1 to 4 carbon atoms. If A is an alkylene group, on the other hand, the number of carbon atoms in the main chain of the alkylene group that inter-bonds phenyl groups should preferably be 2 to 4.

[Chemical 2]

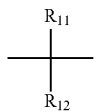

General Formula (5)

(wherein $R_{11}$ and $R_{12}$ are a hydrogen atom or alkyl group with 1 to 8 carbon atoms, where if at least one of $R_{11}$ and $R_{12}$ is an alkyl group, the total number of carbon atoms of $R_{11}$ and $R_{12}$ is 1 to 8)

Specific examples of the alkyl group with 1 to 8 carbon atoms, represented by $R_1$, include a methyl group, ethyl group, propyl group, isopropyl group, sec-butyl group, t-butyl group, cyclopentyl group, cyclohexyl group, t-octyl or other straight-chain, branched-chain or cyclic saturated hydrocarbon group, among others. In addition, specifically the alkoxy group with 1 to 8 carbon atoms should be a methoxy group, ethoxy group, propoxy group, isopropoxy group, butoxy group, t-butoxy group, t-octyl oxy group, etc. A preferred form of $R_1$ is an alkyl group with 1 to 4 carbon atoms, where n should preferably be 0 or 1.

Also regarding the single-ring or condensed-ring aromatic hydrocarbon group with 6 to 15 carbon atoms that may have an aliphatic hydrocarbon group with 1 to 8 carbon atoms in its main chain, represented by $R_2$, the number of carbon atoms of the single-ring or condensed-ring aromatic hydrocarbon group with 6 to 15 carbon atoms should preferably be 6 to 10, and such aromatic hydrocarbon group may be substituted by an alkyl group with 1 to 4 carbon atoms. Specific preferred examples include 1,2-phenylene, 1,3-phenylene, 1,4-phenylene, 2-methyl-1,4-phenylene, 2,6-dimethyl-1,4-phenylene, 2-isopropyl-1,4-phenylene or other single-ring aromatic hydrocarbon group, 1,5-naphthylene, 2,7-naphthylene, anthracene-2,7-diyl, fluorene-2,7-diyl or other condensed-ring aromatic hydrocarbon group.

Also, the single-ring or condensed-ring aromatic hydrocarbon group with 6 to 15 carbon atoms that has an aliphatic hydrocarbon group with 1 to 8 carbon atoms in its main chain, which is another embodiment of $R_2$, is expressed by General Formula (6) below:

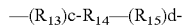  [Chemical 3]

However, the ether group is expressed by the formula below:

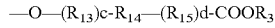  General Formula (6)

In the formula, $R_{13}$ and $R_{15}$ each independently represents an aliphatic hydrocarbon with 1 to 8 carbon atoms, where c and d are 0 or 1, and the total number of carbon atoms of $R_{13}$ and $R_{15}$ is 1 to 8 and c and d are not both 0, but preferably c should be 1 and d should be 0, while $R_{14}$ represents a single-ring or condensed-ring aromatic hydrocarbon group with 6 to 15 carbon atoms.

In General Formula (6) above, the bivalent aliphatic hydrocarbon groups with 1 to 8 carbon atoms, represented by $R_{13}$ and $R_{15}$, are straight-chain or branched-chain saturated or unsaturated hydrocarbon groups with 1 to 8 carbon atoms, where specific examples include methylene, ethylene, ethane-1,1-diyl, propylene, propane-1,1-diyl, butylene, ethyl ethylene, 2-methyl-1,3-propylene, 2-methyl butane-1,4-diyl, pentamethylene, hexamethylene, 1,1,2,2-tetramethyl ethylene, isopropyl methylene, 1,1-diethyl-methylene or other alkylene group or alkylidene group, vinylene, propylene, 2-butenylene, 2-pentenylene or other unsaturated hydrocarbon group.

In addition, the single-ring or condensed-ring aromatic hydrocarbon group with 6 to 15 carbon atoms, represented by $R_{14}$, is the same as the single-ring or condensed-ring aromatic hydrocarbon represented by $R_2$ above. Of these, the aromatic hydrocarbon group $R_{14}$ should preferably be a phenylene group or naphthylene group, while the aliphatic hydrocarbon groups $R_{13}$ and $R_{15}$ should preferably be a saturated hydrocarbon group with 1 to 4 carbon atoms, or more preferably a saturated hydrocarbon group with 1 or 2 carbon atoms.

Also regarding $R_{13}$ in General Formula (6), the carbon atom bonded with the ether group should preferably be a primary or secondary carbon atom for the reason of ensuring stability against acids.

On the other hand, $R_3$ represents a hydrogen atom or alkyl group with 1 to 6 carbon atoms, where the alkyl group with 1 to 6 carbon atoms is a straight-chain, branched-chain or cyclic saturated alkyl group. Specific examples include methyl, ethyl, n-butyl, t-butyl, sec-butyl, isopropyl, n-propyl, cyclohexyl, etc. Preferably, it should be a primary or secondary alkyl group or hydrogen atom.

Accordingly, specific examples of the single-ring or condensed-ring aromatic hydrocarbon with 6 to 15 carbon atoms that has an aliphatic hydrocarbon group with 1 to 8 carbon atoms in the main chain, include the following:

[Chemical 4]

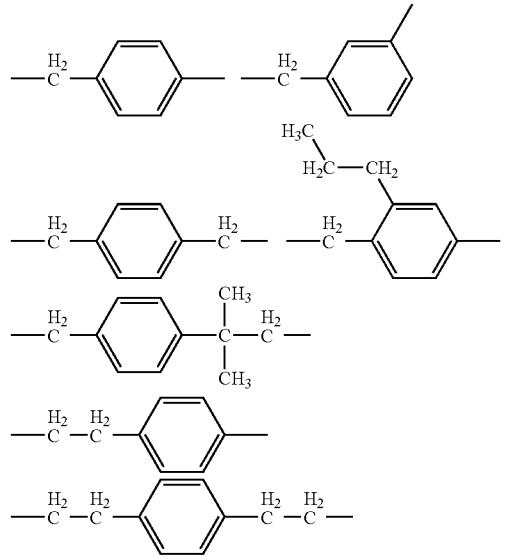

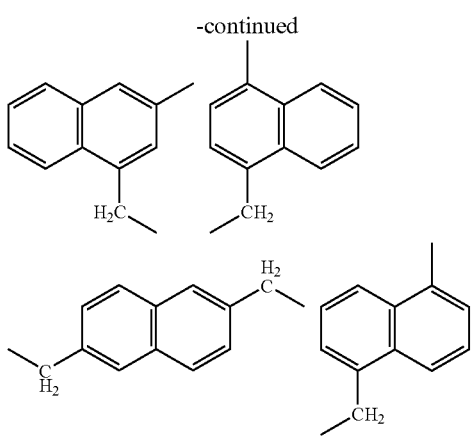

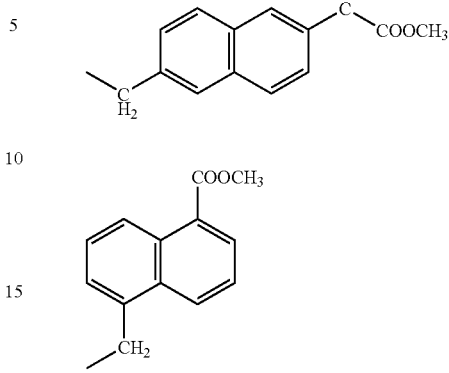

Accordingly regarding a bis(formylphenyl)alkane expressed by General Formula (1), specific examples of the ester substituted hydrocarbon group bonded to the ether group, or specifically the carboxy aromatic hydrocarbon group or alkoxy carbonyl aromatic hydrocarbon group represented by —$R_2COOR_3$, include the following:

Also in General Formula (1), the position of the ether group bonded to the phenyl nucleus at the end should preferably be the o-position or p-position relative to the position of bonding with the saturated aliphatic hydrocarbon group at the center, while the position of the formyl group should preferably be the o-position or p-position relative to the ether group, specific examples of which include those expressed by General Formula (7), (8) or (9) below:

[Chemical 5]

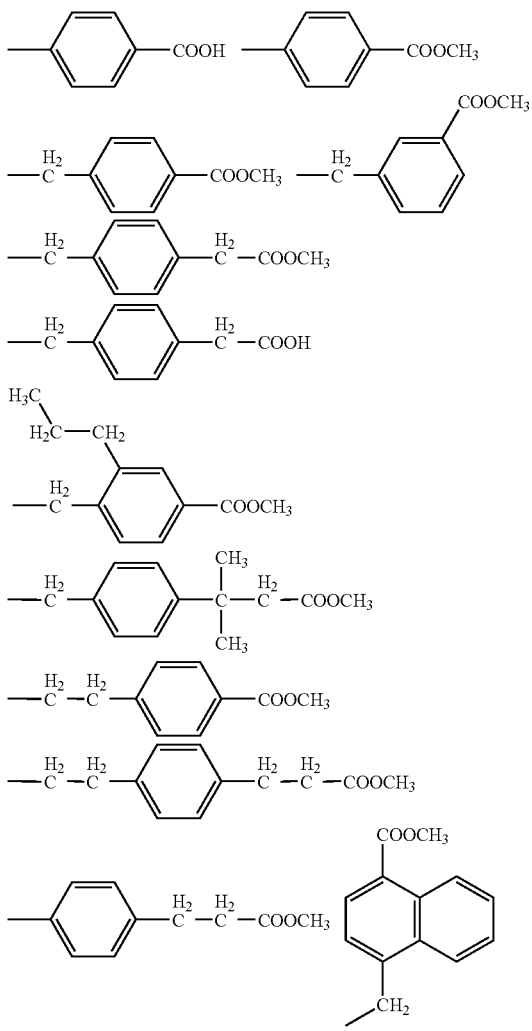

[Chemical 6]

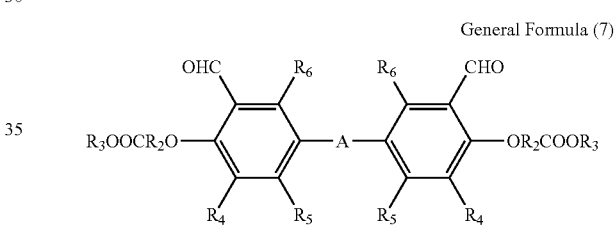

General Formula (7)

(wherein A, $R_2$ and $R_3$ are the same as the corresponding items in General Formula (1), while $R_4$, $R_5$ and $R_6$ are the same as the corresponding items in General Formula (2))

In General Formula (7), preferably at least one of $R_5$ and $R_6$ should be a hydrogen atom or both should be a hydrogen atom. If A is an alkylidene group expressed by General Formula (5) above and both $R_{11}$ and $R_{12}$ are an alkyl group, or if A is an alkylene group and the carbon atom of A bonding with a phenyl group does not bond with a hydrogen atom, then preferably both of $R_5$ and $R_6$ should be a hydrogen atom.

[Chemical 7]

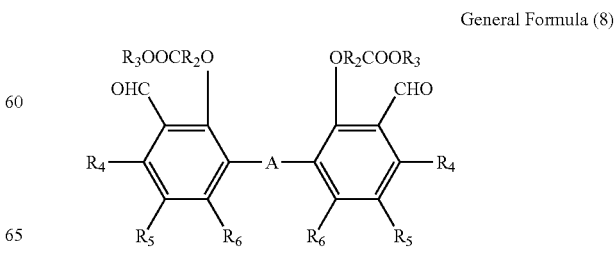

General Formula (8)

[Chemical 8]

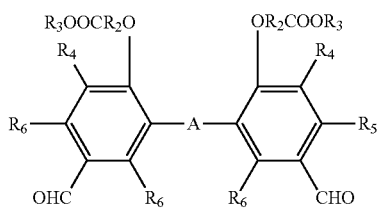

General Formula (9)

(in General Formulas (8) and (9), A, $R_2$ and $R_3$ are the same as the corresponding items in General Formula (1), while $R_4$, $R_5$ and $R_6$ are the same as the corresponding items in General Formula (2))

In General Formulas (8) and (9), preferably at least one of $R_{11}$ and $R_{12}$ should be a hydrogen atom if A is an alkylidene group expressed by General Formula (5) above, where $R_6$ should preferably be a hydrogen atom or primary or secondary alkyl group.

Accordingly, specific examples of a bis(formylphenyl)alkane expressed by General Formula (1) conforming to the present invention include:

bis(3-formyl-4-(4-methoxycarbonylphenyl)methoxyphenyl)methane (Compound 1),

[Chemical 9]

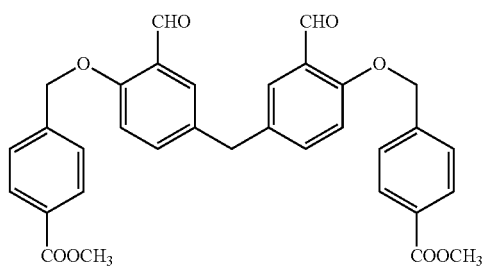

Compound (1)

bis(3-formyl-5-methyl-4-(2-(4-methoxycarbonylphenyl)ethyl)oxyphenyl)methane (Compound 2),

[Chemical 10]

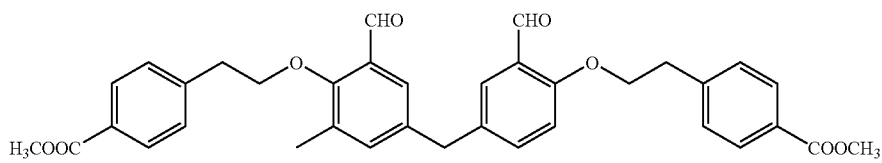

Compound (2)

bis(3-formyl-4-(3-methoxycarbonylphenyl)methoxyphenyl)methane (Compound 3),

[Chemical 11]

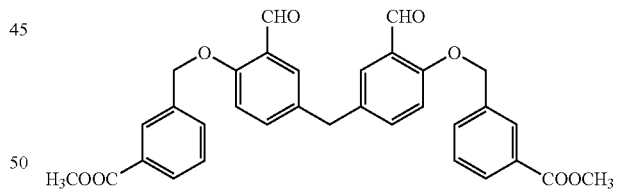

Compound (3)

bis(3-formyl-4-(4-methoxycarbonylphenyl)oxyphenyl)methane (Compound 4),

[Chemical 12]

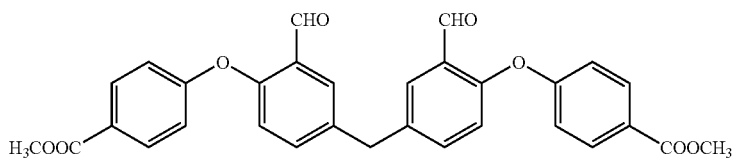

Compound (4)

2,2-bis{3-formyl-4-(4-methoxycarbonylphenyl)
methoxyphenyl}propane (Compound 5),

[Chemical 13]

Compound (5)

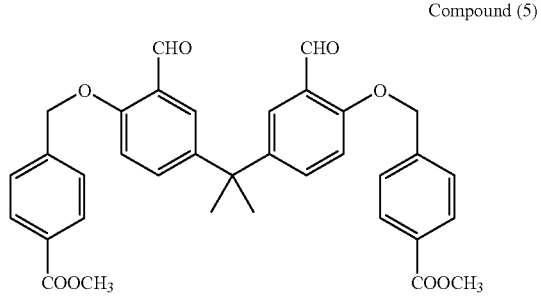

and bis[2-(4-methoxycarbonylphenyl)methoxy-3-formyl-5-methylphenyl]methane (Compound 6).

[Chemical 14]

Compound (6)

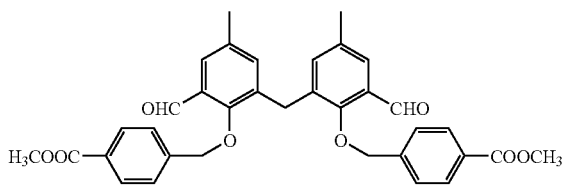

Other examples include bis{3-formyl-4-(2-methoxycarbonylphenyl)oxyphenyl}methane, bis[3-formyl-4-[2-{4-(2-methoxycarbonylethyl)phenyl}ethyl]oxyphenyl]methane, bis[3-formyl-4-(2-{4-(methoxycarbonylmethyl)phenyl}ethyl)oxyphenyl]methane, bis(3-formyl-4-(5-methoxycarbonyl-1-naphthyl)methoxyphenyl)methane, 1,2-bis(3-formyl-4-(4-methoxycarbonylphenyl)methoxyphenyl)ethane, bis(3-formyl-4-(4-carboxyphenyl)methoxyphenyl)methane, and 2,2-bis{3-formyl-4-(4-carboxyphenyl)methoxyphenyl}propane, among others.

These bis(formylphenyl)alkanes expressed by General Formula (1) above, conforming to the present invention, are not specifically limited in terms of how they should be manufactured, and they can be manufactured, for example, as shown in Reaction Formula (1) below, by causing to react with hexamethylene tetramine in the presence of an acid a bis(hydroxymethyl-hydroxyphenyl)alkane expressed by General Formula (10) below and corresponding to the target bis(formylphenyl)alkane, and hydrolyzing the reaction product to obtain a bis(hydroxy-formylphenyl)alkane expressed by General Formula (11) below, and then using this bis(hydroxy-formylphenyl)alkane as a direct material and causing the material to react in the presence of a base with, for example, a halogenated alkoxycarbonyl hydrocarbon expressed by General Formula (12) below, as shown in Reaction Formula (2) below:

[Chemical 15]

Reaction Formula (1)

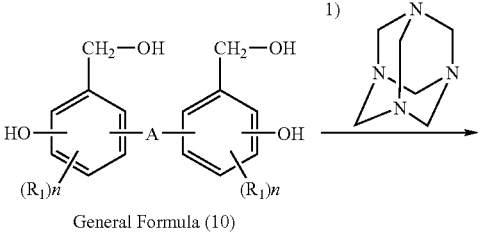

General Formula (11)

In the formula, A, $R_1$ and n are the same as the corresponding items in General Formula (1).

Z—$R_2$COOR$_3$     [Chemical 16]

General Formula (12)

In the formula, Z represents a halogen atom, while $R_2$ and $R_3$ are the same as the corresponding items in General Formula (1).

Also, $R_3$ should preferably be an alkyl group with 1 to 6 carbon atoms, while the halogen atom should preferably be a chlorine atom or bromine atom.

[Chemical 17]

Reaction Formula (2)

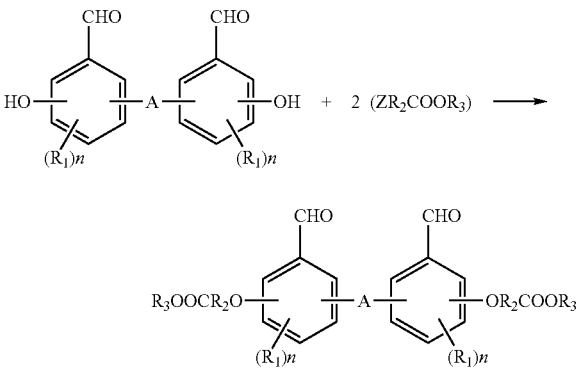

In Reaction Formula (1), with respect to the material bis(hydroxymethyl-hydroxyphenyl)alkane expressed by General Formula (10) above, A, $R_1$ and n in the formula are the same as the corresponding items in General Formula (1).

Accordingly, specific examples of a bis(hydroxymethyl-hydroxyphenyl)alkane expressed by General Formula (10) above include, among others, bis(3-hydroxymethyl-4-hydroxyphenyl)methane, 2,2-bis(3-hydroxymethyl-4-hydroxyphenyl)propane, and 1,2-bis(3-hydroxymethyl-4-hydroxy-5-methoxyphenyl)ethane.

In the aforementioned manufacturing method, the acid to be used when causing a bis(hydroxymethyl-hydroxyphenyl)alkane to react with hexamethylene tetramine in the presence of an acid should preferably be an organic carboxylic acid or boric acid, or more preferably a liquid halogenated organic carboxylic acid.

As for the amount of acid used in the reaction, the range of use amounts or an appropriate amount of acid varies depending on the type of acid. Normally, however, acid should be used in a range of approx. 0.1 to 100 mol, or preferably in a range of approx. 1 to 50 mol, relative to 1 mol of bisphenol. If trifluoroacetic acid is to be used, for example, it should be used in a range of 1 to 30 mol, or preferably in a range of 5 to 20 mol, relative to 1 mol of bis(hydroxymethyl-hydroxyphenyl)alkane.

Also regarding the amount of hexamethylene tetramine used, there are no limitations as long as the amount is at least 2 mol for 1 mol of bis(hydroxymethyl-hydroxyphenyl)alkane. Because using an excessive amount of hexamethylene tetramine will lower the reaction efficiency, however, normally hexamethylene tetramine should be used in a range of 2 to 10 mol, or preferably in a range of 2 to 5 mol, or more preferably in a range of 2.1 to 3 mol.

A solvent may or may not be used in the reaction. No solvent is necessary as long as the reaction composition can be agitated. If the acid or material used has a high melting point or the reaction liquid is very viscous at the reaction temperature, or when agitation is otherwise difficult, however, preferably a solvent should be used.

Examples of solvents to be used include: ether, diethyl ether, tetrahydrofuran and other chain or cyclic aliphatic ethers; ethyl acetate, n-butyl acetate and other aliphatic esters preferably of primary or secondary type; methanol, ethanol, butanol and other lower aliphatic alcohols with a carbon number of 1 to 4; cyclohexanol and other alicyclic alkyl alcohols; toluene, xylene, ethyl benzene and other aromatic hydrocarbons, among others.

At the time of reaction, how to introduce the reacting materials, and the sequence in which they are introduced, are not limited and an appropriate method or sequence may be selected as deemed appropriate according to the properties, etc., of each material used. For example, the material bis(hydroxymethyl-hydroxyphenyl)alkane may be added to a solution in which acid, hexamethylene tetramine and solvent may be present, or acid and hexamethylene tetramine may be added to a solution in which bis(hydroxymethyl-hydroxyphenyl)alkane and solvent may be present, or acid may be added to a solution in which bis(hydroxymethyl-hydroxyphenyl)alkane, hexamethylene tetramine and solvent may be present. If an organic carboxylic acid is used as an acid, a method whereby the material bis(hydroxymethyl-hydroxyphenyl)alkane is added to a solution in which organic carboxylic acid, hexamethylene tetramine and solvent may be present is preferable.

The reaction temperature and pressure are not specifically limited as long as the reaction can be implemented smoothly. However, the reaction temperature should normally be in a range of −50 to 150° C., or preferably in a range of 0 to 110° C., or more preferably in a range of 50 to 90° C. On the other hand, the reaction pressure should be in a range of slight decompression to slight compression, or preferably at around normal pressure.

The intermediate reaction product thus obtained by causing the aforementioned bis(hydroxymethyl-hydroxyphenyl)alkane to react with hexamethylene tetramine in the presence of an acid is hydrolyzed to obtain the target bis(hydroxyformylphenyl)alkane.

In the hydrolysis reaction, the intermediate reaction product obtained through reaction with hexamethylene tetramine may be filtered and separated, or refined further, if necessary. From the viewpoints of reaction efficiency, improvement of yield, etc., however, it is preferable to directly use the above mixture obtained through reaction with hexamethylene tetramine. Also, it is preferable to use a catalyst at the time of reaction. The catalyst to be used should preferably be an acid catalyst and, for example, the acid that was used in the reaction with hexamethylene tetramine may be used directly as the catalyst for hydrolysis, in which case more acid may be added if the reaction is slow.

Or, any known acid catalyst may be added separately. However, exercise caution if a strong acid is used, because if used in an excessive amount it will cause the formyl groups to polymerize and the yield to drop.

The amount of acid used should normally be in a range of 0.1 to 100 mol, or preferably in a range of 1 to 20 mol, relative to 1 mol of bis(hydroxymethyl-hydroxyphenyl)alkane.

Accordingly, the acid catalyst used in hydrolysis may be hydrochloric acid, sulfuric acid or other mineral acid, p-toluene sulfonic acid or other organic sulfone, phosphoric acid, or acetic acid, formic acid, trifluoroacetic acid or other organic carboxylic acid, among others.

Also at the time of hydrolysis reaction, the amount of water in the reaction composition is not specifically limited as long as the reaction can be implemented smoothly. From the viewpoint of reaction efficiency, etc., water should be used normally in a range of 2 to 80 mol, or preferably in a range of 20 to 50 mol, relative to the material bis(hydroxymethyl-hydroxyphenyl)alkane.

The reaction temperature and pressure are not specifically limited as long as the reaction can be implemented smoothly. However, the reaction temperature should normally be in a range of −50 to 150° C., or preferably in a range of 0 to 100° C., or more preferably in a range of 50 to 80° C. On the other hand, the reaction pressure should be in a range of slight decompression to slight compression, or preferably at around normal pressure.

After the reaction, the target crude substance or refined substance can be obtained at a favorable yield from the obtained final reaction mixture by using any known method. If the target substance has precipitated as crystal in the final reaction mixture, for example, the target substance may be filtered directly. If it has not precipitated as crystal, on the other hand, a poor solvent may be added to the final reaction mixture to cause the target substance to precipitate and separate.

At this time, the acid catalyst in the final reaction mixture need not be always neutralized using alkali water. For example, an appropriate amount of aqueous sodium hydroxide solution or other alkali water needed to neutralize the acid catalyst may be added to the final reaction mixture to neutralize it to approx. pH5 to 7, before performing the aforementioned separation/precipitation of the target substance, or alternately the target substance may be precipitated and separated without neutralizing the acid catalyst in the final reaction mixture, after which the obtained crude target substance may be washed with water to remove the acid.

Particularly when the acid used in the reaction is one with a low boiling point such as trifluoroacetic acid, the latter method does not neutralize the acid catalyst in the final reaction product, in which case the acid catalyst may be collected by means of distillation and the collected acid catalyst may be reused directly.

After the aforementioned operations, the target substance is refined, if necessary. To do this, the obtained crude target substance may be dissolved by adding thereto water and toluene, xylene, methyl isobutyl ketone, ether or other solvent separable with water, after which the water layer is separated and the oil layer is washed with water to obtain the oil layer containing the target substance. Next, the solvent is distilled and removed from the obtained oil layer, and then a crystallization solvent is added to crystallize and filter out the target substance in a form of crude crystal. If the purity of crude crystal is low, the aforementioned recrystalization operation may be performed once or multiple times as necessary.

In the aforementioned manufacturing method, the bis(hydroxymethyl-hydroxyphenyl)alkane expressed by General Formula (10), which is used as the material, is not specifically limited in terms of how it should be manufactured. However, it can be easily obtained from a bisphenol corresponding to the target substance, as expressed by General Formula (13) below, by means of any known hydroxy methylation reaction, etc.

[Chemical 18]

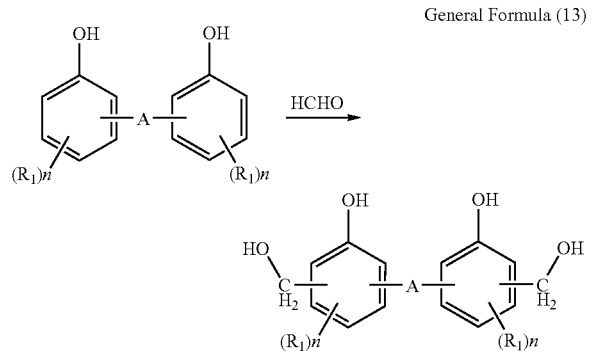

(wherein A, $R_1$ and n are the same as the corresponding items in General Formula (1))

It is more preferable that one of the o-position and p-position relative to the hydroxyl group of the material bisphenol has no substitution group, but there be a substitution group in other positions, because then the yield will improve and product of high purity can be obtained with ease.

In addition, the bis(hydroxy-formylphenyl)alkane expressed by General Formula (11) can also be obtained through hydrolysis after causing a bis(hydroxyphenyl)alkane expressed in General Formula (13) to react with hexamethylene tetramine using the known Duff method, or specifically in the presence of trifluoroacetic acid or other acid, as shown in Reaction Formula (3) below. Other known method may also be used whereby, if A is a methylene group, it is possible to cause formaldehyde polymer constituted by benzaldehyde and formaldehyde or trioxane, etc., to react in the presence of an acid or base catalyst. As for the refining method, any method similar to the one explained above may be used.

[Chemical 19]

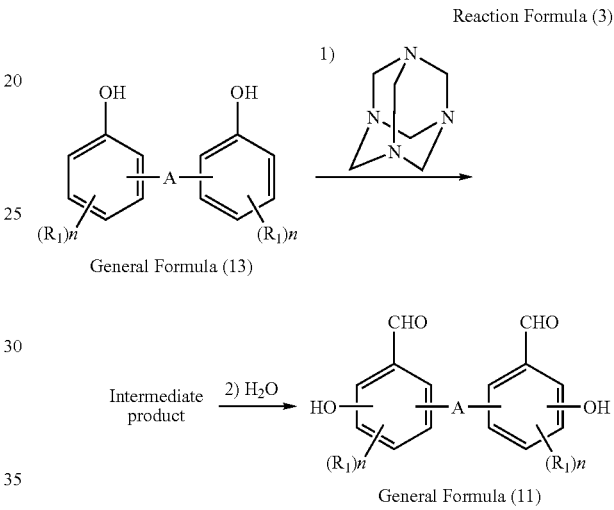

In the formula, A, $R_1$ and n are the same as the corresponding items in General Formula (1).

The manufacturing method based on Reaction Formula (1) is more preferable to the one based on Reaction Formula (3) because the yield is higher.

Accordingly, specific examples of a bis(hydroxy-formylphenyl)alkane expressed by General Formula (11), which is used as a direct material, include, among others, 4,4'-methylene bis(2-formylphenol), 4,4'-methylene bis(6-methyl-2-formylphenol), 2,2'-methylene bis(4-formyl-6-methoxyphenol), 2,2-bis(3-formyl-4-hydroxyphenyl)propane, 2,2-bis(3-formyl-5-t-butyl-4-hydroxyphenyl)propane, and 1,2-bis(3-formyl-5-methoxy-4-hydroxyphenyl)ethane.

By using as a direct material a bis(hydroxy-formylphenyl) alkane expressed by General Formula (11) above which is obtained this way, and causing it to react with a halogenated alkoxycarbonyl hydrocarbon expressed by General Formula (12) above in the presence of a base as shown in Reaction Formula (2) above, a bis(formylphenyl)alkane expressed by General Formula (1) conforming to the present invention can be manufactured.

For example, Reaction Formula (4) below applies to a case where bis[4-(4-methoxycarbonylphenyl)methyl oxy-3-formyl-phenyl]methane is obtained by using bis(4-hydroxy-3-formylphenyl)methane as the bis(hydroxy-formylphenyl) alkane, and using p-chloride methylbenzenecarboxylic acid methyl ester as the halogenated alkoxycarbonyl hydrocarbon.

[Chemical 20]

Reaction Formula (4)

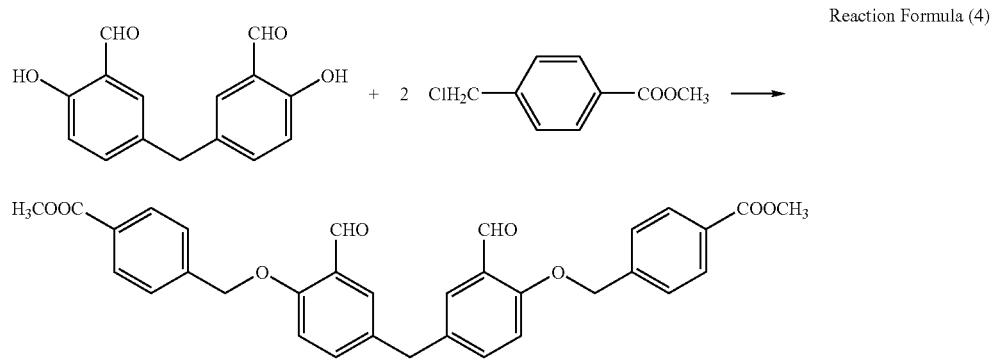

Under the manufacturing method illustrated by Reaction Formula (4), it is sufficient only to cause a bis(hydroxy-formylphenyl)alkane to react with a halogenated alkoxycarbonyl hydrocarbon in the presence of potassium carbonate or other base in a reaction solvent such as dimethyl formamide, etc.

The base to be used may be an organic base or inorganic base. If an organic base is used, however, preferred examples include tetramethyl ammonium hydroxide or other hydroxy quaternary amine, and 1,8-diazabicyclo[5.4.0]undec-7-en (abbreviated as "DBU"), among others.

If an inorganic base is used, on the other hand, preferred examples include sodium hydroxide, potassium hydroxide and other alkali metal hydroxides, potassium carbonate, sodium carbonate and other alkali metal carbonate salts, hydrogenated sodium, hydrogenated potassium, hydrogenated lithium and other hydrogenated alkali metals, and t-butoxy potassium and other alkoxy alkali metals, among others.

The additive amount of such base should normally be in a range of 2 to 3 mol, or preferably in a range of 2.2 to 2.7 mol, relative to 1 mol of a bis(hydroxy-formylphenyl)alkane expressed by General Formula (11).

The solvent used in the reaction should preferably be, for example, dioxane, THF or other ether, dimethyl formamide, dimethyl acetamide or other amide, dimethyl sulfoxide, hexamethylene phosphonic acid amide, pyridine, 4-methyl pyridine, N-methyl pyrrolidone or other amine, or any mixture of the foregoing.

From the viewpoint of reaction volume efficiency, etc., the amount of solvent used should normally be in a range of 1 to 10 parts by weight, or preferably in a range of 2 to 5 parts by weight, relative to 1 part by weight of the material bis(hydroxy-formylphenyl)alkane.

Also, potassium iodide or other alkali metal iodide, copper, copper chloride or other copper compound, phase transfer catalyst or other reaction accelerating additive may be added to accelerate the etherification reaction as necessary.

At the time of reaction, how to introduce the reacting materials, and the sequence in which they are introduced, are not limited. Normally, however, a method whereby a bis(hydroxy-formylphenyl)alkane expressed by General Formula (11) is mixed with a base to produce an oxy salt, and then a halogenated alkoxycarbonyl hydrocarbon expressed by General Formula (12) is added to this mixture, is preferred because it leads to higher yields.

The reaction should be performed at temperatures normally in a range of 20 to 200° C., or preferably in a range of 50 to 120° C., for several hours such as 2 to 20 hours. On the other hand, the reaction pressure should normally be in a range of slight decompression to slight compression, or preferably at around normal pressure.

After the reaction, an appropriate amount of organic solvent, such as toluene, cyclohexane, etc., is added, together with water, to the reaction mixture for the purpose of washing and separation, and if necessary the organic layer is washed with an aqueous acid solution to neutralize the organic layer and then the solvent is distilled and removed from the organic layer, after which methanol or other aliphatic lower alcohol, or if necessary toluene or other aromatic hydrocarbon or methyl ethyl ketone or other aliphatic ketone, is added to the residue to crystallize or filter out the target substance, or otherwise the solvent is distilled and removed from the organic layer containing the target substance, in order to obtain the target substance under the present invention, or specifically a bis(formylphenyl)alkane expressed by General Formula (1). After the reaction, an appropriate amount of water may be added to dissolve the inorganic salt, if the target crystal has precipitated, after which a solvent may be added, if necessary, or the mixture may be cooled directly to filter out the target substance.

With respect to a bis(formylphenyl)alkane expressed by General Formula (1), the manufacturing method to obtain the carboxy hydrocarbon oxy substitution product, when $R_3$ is a hydrogen atom, is not specifically limited. However, it is possible to obtain a carboxy hydrocarbon group ($-R_2COOH$) substitution product with ease by, for example, hydrolyzing the bis(formylphenyl)alkane obtained above in the presence of an alkali and then producing a substitution product where $R_3$ in the hydrocarbon group ($-R_2COOR_3$) bonding with the ether group is a primary or secondary alkyl group. For example, a bis[4-(4-carboxyphenyl)-methoxy-3-formyl-phenyl]methane can be obtained by hydrolyzing in the presence of an alkali a bis[4-(4-methoxycarbonylphenyl)-methoxy-3-formyl-phenyl]methane obtained according to Reaction Formula (4) above, as shown in Reaction Formula (5) below:

[Chemical 21]

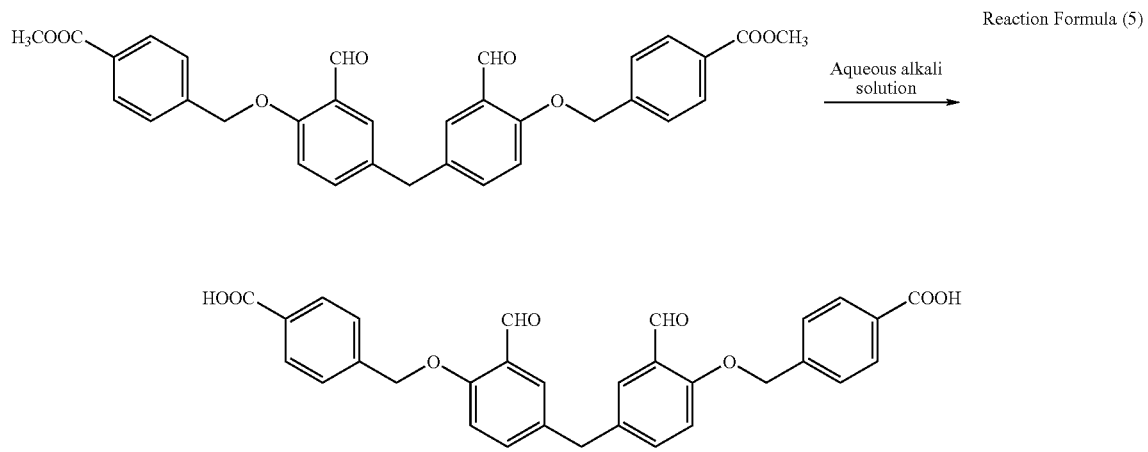

Reaction Formula (5)

If R₃ in the bis(formylphenyl)alkane compound illustrated by Reaction Formula (5) above is a hydrogen atom, then in the manufacturing method of bis(formylphenyl)alkane where an alkoxycarbonyl aromatic hydrocarbon group is hydrolyzed and converted into a carboxy aromatic hydrocarbon group, it is preferable that $R_3$ in the alkoxycarbonyl aromatic hydrocarbon group (—$R_2COOR_3$) of the material bis(formylphenyl)alkane be a primary or secondary alkyl group, where a primary alkyl group is preferable because then the hydrolysis reaction becomes easy as in any known hydrolysis reaction involving ester groups.

Accordingly, a carboxy aromatic hydrocarbon substitution product can be obtained easily by hydrolyzing such bis(formylphenyl)alkane using sodium hydroxide, tetramethyl ammonium hydroxide or other aqueous alkali solution.

The aqueous alkali solution used in the hydrolysis reaction should preferably be sodium hydroxide, potassium hydroxide or other inorganic aqueous strong alkali solution, or tetramethyl ammonium hydroxide or other organic aqueous strong alkali solution, where the alkali concentration should be in a range of 5 to 50%, or preferably in a range of 10 to 30%. The amount of alkali used should normally be in a range of 2 to 6 mol, or preferably in a range of 2 to 4 mol, relative to 1 mol of the material bis(formylphenyl)alkane. The reaction temperature is normally in a range of 0 to 100° C., or preferably in a range of 10 to 50° C. Under these reaction conditions, the reaction normally ends in approx. 0.5 to 10 hours.

After the reaction, the reaction product may be refined according to a known method, or product of high purity may be obtained, if necessary.

Next, a polynuclear phenol derived from the aforementioned bis(formylphenyl)alkane, which is another novel compound proposed by the present invention, is expressed by General Formula (2) below.

A polynuclear polyphenol expressed by General Formula (2) below:

[Chemical 22]

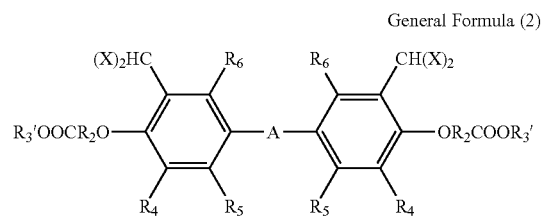

General Formula (2)

(wherein A and $R_2$ are the same as the corresponding items in General Formula (1) above, $R_4$, $R_5$ and $R_6$ each independently represent a hydrogen atom, alkyl group with 1 to 8 carbon atoms or alkoxy group with 1 to 8 carbon atoms, $R_3'$ represents a hydrogen atom or primary or secondary alkyl group with 1 to 6 carbon atoms, and X represents a hydroxyphenyl group expressed by General Formula (3) below)

[Chemical 23]

General Formula (3)

(wherein $R_7$ represents a hydrogen atom, alkyl group with 1 to 8 carbon atoms or alkoxy group with 1 to 8 carbon atoms, a represents an integer of 1 to 3, and b represents an integer of 0 to 4, with a proviso that $1 \geq a+b \geq 5$ wherein if b is 2 or greater, each $R_7$ may be the same or different)

Also in General Formula (3) above, a preferred hydroxyphenyl group is expressed by General Formula (4) below:

[Chemical 24]

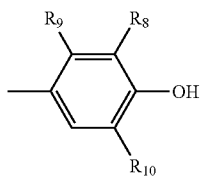

General Formula (4)

(wherein $R_8$, $R_9$ and $R_{10}$ are each independently the same as $R_7$ in General Formula (3))

In General Formula (2) above, specific examples of the saturated aliphatic hydrocarbon group with 1 to 9 carbon atoms, represented by A, are the same as the corresponding examples pertaining to General Formula (1). Also when A is an alkylidene group according to General Formula (5) above, $R_{11}$ and $R_{12}$ should preferably be a hydrogen atom or primary or secondary alkyl group, or more preferably a hydrogen atom or alkyl group with 1 to 4 carbon atoms, which is the same as under General Formula (1). If A is an alkylene group, the number of carbon atoms in the main chain of the alkylene group that inter-bonds phenyl groups should preferably be 2 to 4.

Also, it is preferable that at least one of $R_5$ and $R_6$ be a hydrogen atom, or both be a hydrogen atom. If A is an alkylidene group according to General Formula (5) above and $R_{11}$ and $R_{12}$ are both an alkyl group, or if A is an alkylene group and the carbon atom of A bonding with a phenyl group is not bonding with a hydrogen atom, preferably $R_5$ and $R_6$ should both be a hydrogen atom.

In the formula, the embodiments, specific examples and preferred groups of the aliphatic hydrocarbon group represented by $R_2$ are the same as the corresponding items in General Formulas (1) and (6).

As for $R_4$, $R_5$ and $R_6$, the embodiments and specific examples of the alkyl group with 1 to 8 carbon atoms or alkoxy group with 1 to 8 carbon atoms are the same as the corresponding items pertaining to $R_1$ in General Formula (1), where an alkyl group with 1 to 4 carbon atoms is preferred.

Also regarding $R_3'$, the primary or secondary alkyl group with 1 to 6 carbon atoms is a straight-chain, branched-chain or cyclic saturated alkyl group, where specific examples include methyl, ethyl, n-butyl, sec-butyl, isopropyl, n-propyl, cyclohexyl, etc.

In General Formulas (3) and (4) above, $R_7$ as well as $R_8$, $R_9$ and $R_{10}$ represent a hydrogen atom, straight-chain, branched-chain or cyclic alkyl group with 1 to 8 carbon atoms, or straight-chain, branched-chain or cyclic alkoxy group with 1 to 8 carbon atoms.

Accordingly, specific examples of a substituted phenyl group expressed by General Formulas (3) and (4) include those having one hydroxyl group such as 4-hydroxyphenyl group, 3-methyl-4-hydroxyphenyl group, 2-methyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 3-t-butyl-6-methyl-4-hydroxyphenyl group, 3,5-di-t-butyl-4-hydroxyphenyl group, 3-sec-butyl-4-hydroxyphenyl group, 3-t-octyl-4-hydroxyphenyl group, 3-t-butyl-5-methyl-4-hydroxyphenyl group, 3-cyclohexyl-4-hydroxyphenyl group, 2-methyl-5-cyclohexyl-4-hydroxyphenyl group, 5-methyl-2-hydroxyphenyl group, 4,6-dimethyl-2-hydroxyphenyl group, 3,4,6-trimethyl-2-hydroxyphenyl group, 3,5-di-t-butyl-2-hydroxyphenyl group, 5-t-octyl-2-hydroxyphenyl group, 3-methoxy-4-hydroxyphenyl group, 5-methyl-2-methoxy-4-hydroxyphenyl group, 3-n-hexyloxy-4-hydroxyphenyl group, 3-n-octyloxy-4-hydroxyphenyl group, and 5-butoxy-2-hydroxyphenyl group, among others, as well as those having two or three hydroxy groups such as 3,4-dihydroxyphenyl group, 2-methyl-4,5-dihydroxyphenyl group, 3-methyl-4,5-dihydorxyphenyl group, 5-methyl-2,4-dihydroxyphenyl group, and 2,3,4-trihydroxyphenyl group, among others.

Accordingly, specific examples of a polynuclear phenol expressed by General Formula (2) include:

bis(3-bis(2,5-dimethyl-4-hydroxyphenyl)methyl-4-(4-carboxyphenyl)methoxyphenyl)methane,

[Chemical 25]

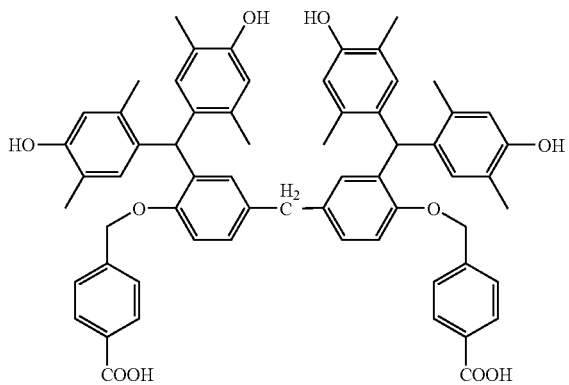

bis(3-bis(3-methyl-4-hydroxyphenyl)methyl-4-(4-carboxyphenyl)methoxyphenyl)methane,

[Chemical 26]

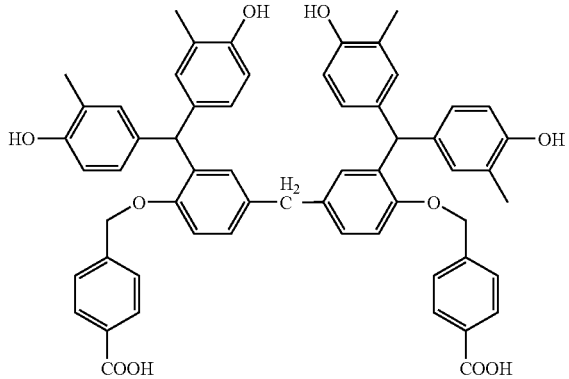

bis(3-bis(2,3,5-trimethyl-4-hydroxyphenyl)methyl-4-(4-carboxyphenyl)methoxyphenyl)methane,

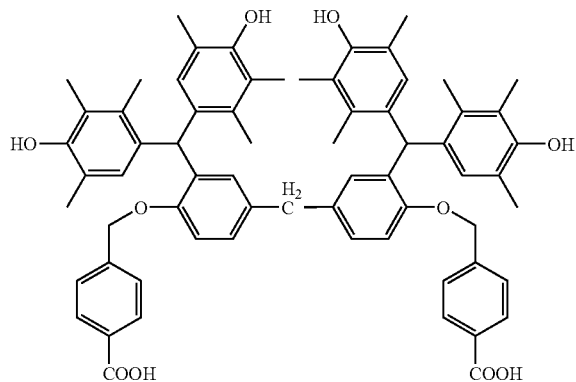

bis(3-bis(2-methyl-5-cyclohexyl-4-hydroxyphenyl)methyl-4-(4-carboxyphenyl)methoxyphenyl)methane,

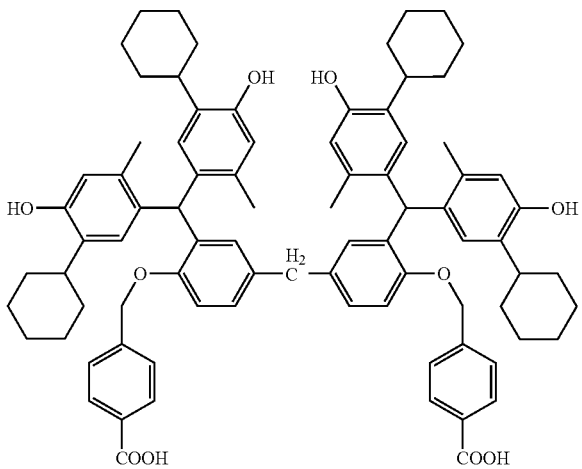

2,2-bis(3-bis(2,5-dimethyl-4-hydroxyphenyl)methyl-4-(4-carboxyphenyl)methoxyphenyl)propane,
2,2-bis(3-bis(2,5-dimethyl-4-hydroxyphenyl)methyl-4-(4-carboxyphenyl)methoxy-5-methylphenyl)propane,
1,2-bis(3-bis(2,5-dimethyl-4-hydroxyphenyl)methyl-4-(4-carboxyphenyl)methoxyphenyl)ethane,
bis(3-bis(5-methyl-2-hydroxyphenyl)methyl-4-(4-carboxyphenyl)methoxyphenyl)methane,
bis(3-bis(4,6-dimethyl-2-hydroxyphenyl)methyl-4-(4-carboxyphenyl)methoxyphenyl)methane,
bis(3-bis(2-methyl-4,5-dihydroxyphenyl)methyl-4-(4-carboxyphenyl)methoxyphenyl)methane, and
bis(3-bis(2,3,4-trihydroxyphenyl)methyl-4-(4-carboxyphenyl)methoxyphenyl)methane, among others.

A polynuclear phenol derived from such bis(formylphenyl)alkane expressed by General Formula (1) above, which is another novel compound proposed by the present invention, is not specifically limited in terms of how it should be manufactured, but it can be obtained through a preferred method whereby, for example, a bis(formylphenyl)alkane expressed by General Formula (7) and conforming to the present invention is used as a direct material and this direct material is caused to react in the presence of an acid catalyst with a phenol corresponding to the hydroxyphenyl group in General Formula (3) or (4) above, as shown in Reaction Formula (7) below, in the case of a reaction involving bis(3-formyl-4-(4-methoxycarbonylphenyl)methoxyphenyl)methane and 2,5-dimethylphenol.

[Chemical 29]

Reaction Formula (7)

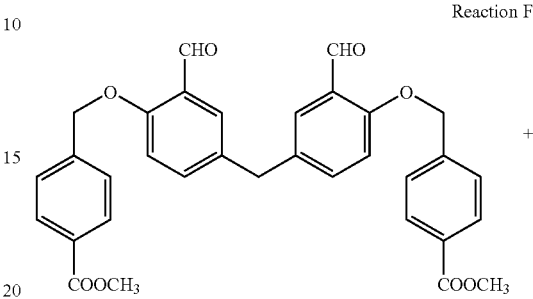

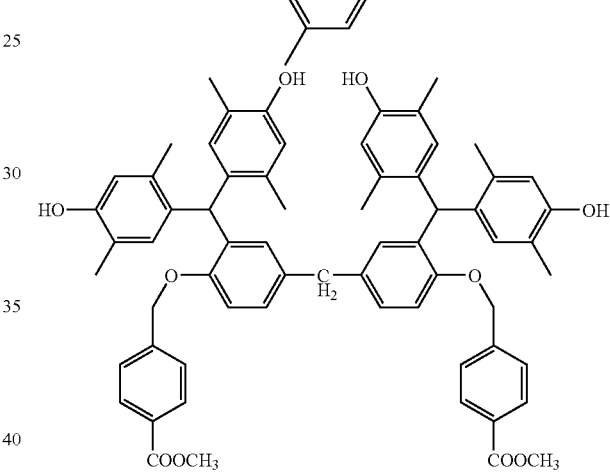

The phenol used above must have at least one of the o-position and p-position of the phenyl nucleus relative to the hydroxy group substituting the phenyl group, not substituted. To be specific, it is preferable, from the viewpoint of synthesis to use a phenol whose p-position relative to the hydroxy group is not substituted if the number of alkyl and/or alkoxyl substitution groups is 3 or less, or use a phenol whose o-position relative to the hydroxy group is not substituted if the number of alkyl and/or alkoxyl substitution groups is 4.

Specific examples of such phenols include those having one hydroxy group such as phenol, o-cresol, p-cresol, m-cresol, 2,5-xylenol, 2,6-xylenol, 3,5-xylenol, 2,3,6-trimethyl phenol, 2,3,5-trimethyl phenol, 2-cyclohexyl-5-methyl phenol, 2-cyclohexyl phenol, 2-ethyl phenol, 2-t-butyl phenol, 2-t-butyl-5-methyl phenol, 2,4-xylenol, 2,6-di-t-butyl phenol, 2,4-di-t-butyl phenol, 2-sec-butyl phenol, 2-n-octyl phenol, 2-t-octyl phenol, 4-t-octyl phenol, 2-isopropyl phenol, 2-t-butyl-4-methyl phenol, 2-methoxy phenol, 2-methyl-5-methoxy phenol, 4-butoxy phenol, 2-n-hexyl oxy phenol, and 2-n-octyl oxy phenol, among others, as well as those having two or more hydroxy groups such as resorcin, catechol, hydroquinone, 4-methyl catechol, 3-methyl catechol, 2-methyl resorcinol, 4-methyl resorcinol, and pyrogallol, among others.

As illustrated by Reaction Formula (7) above, the amount of phenol used in the reaction of bis(formylphenol)alkane and phenol, or specifically the range of preferred amounts relative to 1 mol of bis(formylphenol)alkane, varies depending on the type of phenol used. However, the range is normally 4 to 20 mol, or preferably 4.5 to 10 mol.

Also, a reaction solvent may or may not be used. However, use of a solvent is preferable if the molar ratio of phenol to bis(formylphenyl)alkane is small, or the melting point of phenol is high, or otherwise agitation is difficult. Examples of the reaction solvent used include methanol, butanol and other lower aliphatic alcohols, toluene, xylene and other aromatic hydrocarbons, methyl isobutyl ketone and other aliphatic ketones, and solvents constituted by a mixture of the foregoing. A lower aliphatic alcohol is preferred among the above, and if catechol, resorcin or other phenol having a high melting point and high solubility in water is used, water may be used as a reaction solvent.

Although there are no specific limitations, these solvents are used normally in a range of 0.1 to 10 parts by weight, or preferably in a range of 0.5 to 2 parts by weight, relative to the phenol used.

Under the manufacturing method illustrated by Reaction Formula (7) above, the acid catalyst should preferably be an acid that dissolves in the reaction mixture, and accordingly an inorganic acid or organic sulfonic acid, carboxylic acid or other organic acid of varying acidity from strong to moderate should be used. Specific examples include 35% hydrochloric acid, hydrogen chloride gas, sulfuric acid, phosphoric acid and other inorganic acids, as well as p-toluene sulfonic acid, methane sulfonic acid, oxalic acid and other organic acids. Although a preferred range of amounts used varies depending on the acidity, these acid catalysts are used normally in a range of 1 to 50 percent by weight relative to the phenol.

The reaction should be implemented at temperatures normally in a range of 0 to 100° C., or preferably in a range of 20 to 60° C., in air, or more preferably in an ambience of nitrogen or other inert gas, under agitation, normally for approx. 1 to 20 hours.

Under the aforementioned manufacturing method, the polynuclear phenol compound produced by the reaction may be separated and refined, as necessary, according to any known method.

Accordingly, after the reaction the obtained reaction liquid is mixed with an aqueous sodium hydroxide solution or other alkali water to neutralize the acid, to which toluene, xylene, methyl isobutyl ketone, ether or other solvent separable from water is added, as necessary, to remove the water layer, and then the water layer is separated while the oil layer is washed with water and the solvent and unreacted material phenol are distilled and removed from the obtained oil layer, if necessary, after which a solvent is added to cause crystallization or precipitation, followed by filtering, to obtain crystalline or non-crystalline solids. If necessary, a similar crystallization or precipitation operation may be performed once or multiple times to obtain the target substance of higher purity.

If the polynuclear phenol compound which is the target reaction product is difficult to obtain by means of the aforementioned crystallization or precipitation, it can be obtained and refined by means of column separation. Alternately in the aforementioned refining process, the solvent may be distilled or otherwise removed from the oil layer in which the compound is dissolved, in order to obtain the target substance as a resinous composition.

Also regarding the polynuclear phenol compound expressed by General Formula (2) above, there are no limitations as to the manufacturing method used to obtain a carboxy hydrocarbon oxy substitution product from an ether group when $R_3'$ is a hydrogen atom. As illustrated by Reaction Formula (8) below, for example, the carboxy hydrocarbon oxy substitution product (—O—$R_2$COOH) can be obtained easily from the ether group in the polynuclear phenol compound by means of ester hydrolysis using sodium hydroxide, tetramethyl ammonium hydroxide or other aqueous alkali solution under methods similar to the one used for bis(formylphenyl)alkane explained above.

[Chemical 30]

Reaction Formula (8)

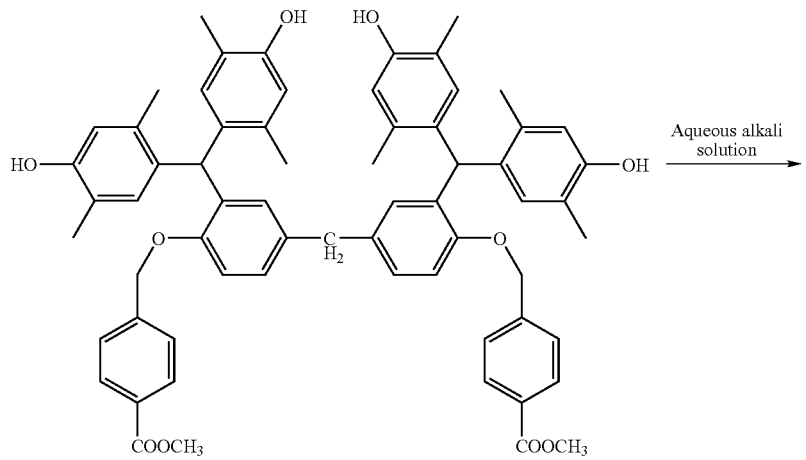

-continued

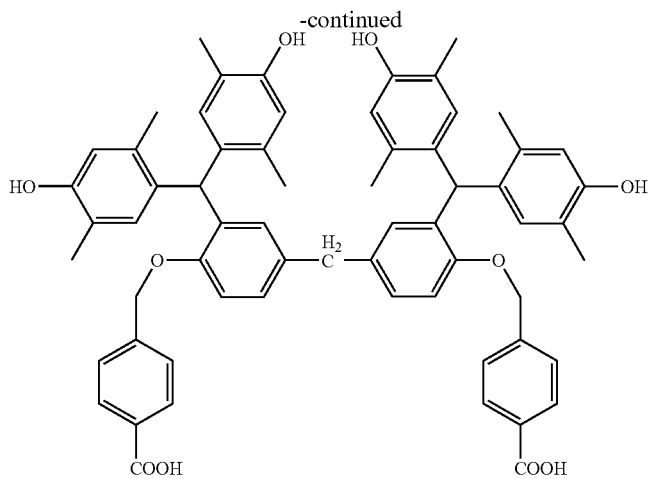

Also, the obtained reaction product may be refined according to any known method to achieve product of high purity, if necessary. For example, after the hydrolysis reaction an aqueous organic acid or inorganic acid solution may be added to neutralize the alkali to adjust the pH to approx. 1 to 4, after which a solvent that separates from water may be added, if necessary, to separate the water layer and then the obtained oil layer is washed with water, followed by the aforementioned methods to isolate and refine the target substance. In this case, it is also preferable that $R_3'$ in the alkoxycarbonyl aromatic hydrocarbon group (—$R_2COOR_3'$) be a primary alkyl group, as is the case with the aforementioned bis(formylphenyl) alkane, because then the hydrolysis reaction becomes easily.

EFFECTS OF THE INVENTION

A bis(formylphenyl)alkane conforming to the present invention has a phenyl nucleus substitution group which includes a formyl group as well as an ether group bonded by a carboxy substituted aromatic hydrocarbon group or alkoxycarbonyl substituted aromatic hydrocarbon group, and therefore it offers excellent heat resistance along with excellent reactivity with phenols due to its formyl group, and excellent reactivity due to the ester group or carboxyl group at the end, and accordingly it is useful as a modifier for phenol resins, etc., photoresist material, intermediate material for various polynuclear phenol compounds obtained through reaction with phenols, or reactive intermediate material for making polynuclear aromatic compounds, etc., that offer excellent heat resistance, among others.

Also, a polynuclear phenol compound, obtained by using as the material a novel bis(formylphenyl)alkane conforming to the present invention, has an ether group as a phenyl nucleus substitution group and thus exhibits excellent heat resistance, represented by high glass transition temperature, etc., and it also contains two highly reactive carboxyl groups or ester groups as well as at least four phenolic hydroxyl groups in the molecule, and due to the selective reactivity and other interaction of these groups, this compound can be expected to demonstrate excellent effects, such as improved resolution, if used as a photosensitive resist or its material. Also, such polynuclear phenol compound is also useful as a material or hardener for epoxy resins, color development agent or anti-fade agent used in thermosensitive recording materials, bactericide, fungicide, antioxidant, etc.

EXAMPLES

The present invention is explained in further details using examples.

Example 1

Synthesis of bis[3-formyl-4-(4-methoxycarbonylphenyl)methoxyphenyl]methane 160.0 g (0.625 mol) of 4,4'-methylene bis(2-formylphenol) and 480 g of N-methyl pyrrolidone were introduced into a four-way flask of 3 liters in capacity equipped with a thermometer, cooling unit and agitator, and the mixture was heated to a temperature of 50° C. and then 207.0 g (1.50 mol) of potassium carbonate powder was added intermittently over a period of 30 minutes under agitation. After the entire amount of potassium carbonate powder was added, the reaction was performed under agitation for further 30 minutes at the same temperature. Thereafter, 276.0 g (1.50 mol) of 4-chloromethyl benzoic acid methyl dissolved in 800 g of N-methyl pyrrolidone was dripped into the obtained solution at a temperature of 50° C. over a period of 2 hours (crystal precipitated in the middle). After the entire amount of N-methyl pyrrolidone was dripped, the temperature was raised to 110° C. over a period of 1 hour and then the reaction was performed for further 7 hours under agitation.

After the reaction, the temperature was lowered to 70° C. and then 200 g (3.333 mol) of acetic acid was dripped over a period of 1 hour. After the entire amount of acetic acid was dripped, the temperature was lowered to 55° C. and then 1,000 g of water was added and the temperature was raised to 70° C. Thereafter, the final reaction mixture was cooled to cause crystallization and the precipitated crystal was filtered out at a temperature of 22° C. At this time, 300 g of methanol, 600 g of water and again 300 g of methanol were added, in this order, to the filtered crystal to wash the crystal. The obtained crystal was dried to obtain the target substance as 314.0 g of white powder (purity by high-speed liquid chromatography: 97.2%). The yield relative to the material 4,4'-methylene bis(2-formylphenol) was 91.0%.

Melting point (peak top value by differential scanning calorimetry): 224.0° C.

Molecular weight (liquid chromatography mass spectrometry/atmospheric pressure chemical ionization method): 551 (M-H)⁻

Proton NMR analysis (400 MHz, solvent: DMSO-d6, reference substance: tetramethyl silane)

TABLE 1

[Chemical 31]

| Chemical shift (ppm) | Proton integration value | Signal | Assignment | Assignment position |
|---|---|---|---|---|
| 10.42 | 2 H | s | —CHO | (a) |
| 7.99 | 4 H | d | Ph-H | (b) |
| 7.64 | 4 H | d | Ph-H | (c) |
| 7.56 | 2 H | s | Ph-H | (d) |
| 7.53 | 2 H | d | Ph-H | (e) |
| 7.23 | 2 H | d | Ph-H | (f) |
| 5.35 | 4 H | s | —CH$_2$— | (g) |
| 3.94 | 2 H | s | —CH$_2$— | (h) |
| 3.85 | 6 H | s | —CH$_3$ | (i) |

Example 2

Synthesis of bis[3-bis(2,5-dimethyl-4-hydroxyphenyl)methyl-4-(4-carboxyphenyl)methoxyphenyl]methane 53.7 g (0.440 mol) of 2,5-xylenol and 53.7 g of methanol were introduced into a four-way flask of 2 liters in capacity equipped with a thermometer, cooling unit and agitator, and 31.5 g of hydrochloric acid gas was blown in at a temperature of 40° C., after which a solution produced by dissolving 80.5 g (0.660 mol) of 2,5-xylenol in 80.5 g of methanol was dripped under agitation. After the entire amount of methanol was dripped, 121.4 g (0.220 mol) of bis(3-formyl-4-(4-methoxycarbonylphenyl)methoxyphenyl)methane powder obtained in Example 1 was added intermittently at a temperature of 40° C. over a period of 2 hours and 30 minutes. After the entire amount of bis(3-formyl-4-(4-methoxycarbonylphenyl)methoxyphenyl)methane powder was added, post-reaction was performed further under agitation for 6 hours at the same temperature.

After the reaction, 16% aqueous sodium hydroxide solution was dripped into the final reaction mixture to neutralize the mixture, and then the obtained solution was condensed at normal pressure until the temperature reached 95° C. The obtained condensed liquid was mixed with 430.0 g of methyl isobutyl ketone and 100.0 g of pure water at a temperature of 80° C. and the mixture was agitated for 30 minutes, after which the water layer was removed and pure water was added further to the obtained oil layer, followed by two cycles of water wash and separation using similar operations. Thereafter, 480.5 g (1.32 mol) of 25% aqueous tetramethyl ammonium hydroxide solution and 72.1 g of pure water were added to the obtained oil layer at a temperature of 50° C., after which methyl ester hydrolysis reaction was performed for 1 hour under agitation. After the hydrolysis, the oil layer was separated and 430.0 g of methyl isobutyl ketone was added to the water layer obtained, after which 35% hydrochloric acid was added at 50° C. to neutralize the mixture. After the neutralization, the temperature was raised to 70° C. to separate the water layer, and pure water was added further to the obtained oil layer, followed by three cycles of water wash and separation using similar operations.

Thereafter, the obtained oil layer was condensed at normal pressure to distill and remove the solvent (crystal precipitated in the middle), after which toluene was added and the mixture was cooled. The cooled mixture was filtered to obtain crude crystal. This crude crystal was dissolved in methyl isobutyl ketone and the obtained oil layer was washed with water, after which the solvent was distilled and removed using an operation similar to the one explained above, and then toluene was added to cause crystallization, followed by cooling. The precipitated crystal was filtered and dried to obtain the target substance as 193.2 g of yellow-orange powder (purity by high-speed liquid chromatography: 98.0%). The yield relative to the material bis(3-formyl-4-(4-methoxycarbonylphenyl)methoxyphenyl)methane was 89.9%.

Melting point (peak top value by differential scanning calorimetry): 231.4° C., 219.4° C.

Molecular weight (liquid chromatography mass spectrometry/atmospheric pressure chemical ionization method): 976 (M-H)⁻

Proton NMR analysis (400 MHz, solvent: DMSO-d6, reference substance: tetramethyl silane)

TABLE 2

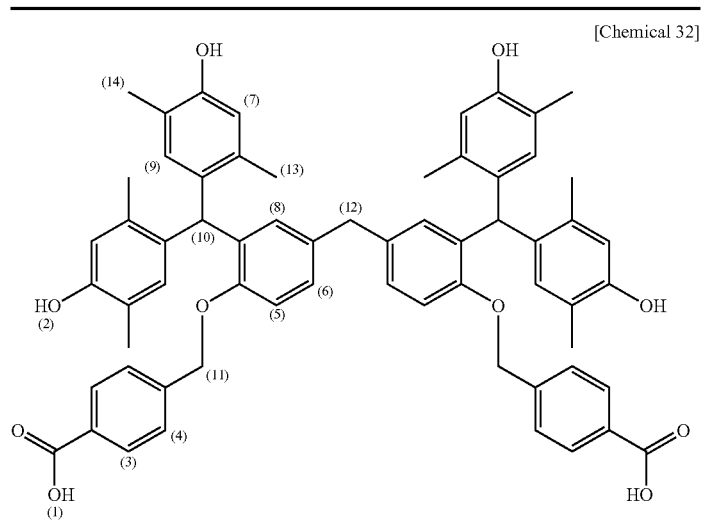

| Chemical shift (ppm) | Proton integration value | Signal | Assignment | Assignment position |
|---|---|---|---|---|
| 12.96 | 2 H | m | —COOH | (1) |
| 8.95 | 4 H | s | —OH | (2) |
| 7.86 | 4 H | d | Ph-H | (3) |
| 7.17 | 4 H | d | Ph-H | (4) |
| 6.90 | 2 H | d | Ph-H | (5) |
| 6.82 | 2 H | dd | Ph-H | (6) |
| 6.62 | 4 H | s | Ph-H | (7) |
| 6.50 | 2 H | d | Ph-H | (8) |
| 6.37 | 4 H | s | Ph-H | (9) |
| 5.74 | 2 H | s | >CH— | (10) |
| 5.06 | 4 H | s | —CH$_2$— | (11) |
| 3.60 | 2 H | s | —CH$_2$— | (12) |
| 1.94 | 12 H | s | —CH$_3$ | (13) |
| 1.90 | 12 H | s | —CH$_3$ | (14) |

What is claimed is:

1. A bis(formylphenyl)alkane expressed by General Formula (1) below:

General Formula (1)

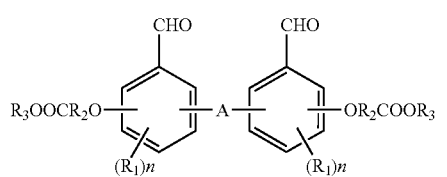

wherein A represents a saturated aliphatic hydrocarbon group with 1 to 9 carbon atoms, each $R_1$ independently represents a hydrogen atom, alkyl group with 1 to 8 carbon atoms or alkoxy group with 1 to 8 carbon atoms, n represents an integer of 0 to 3, $R_2$ represents a single-ring or condensed-ring aromatic hydrocarbon group with 6 to 15 carbon atoms that may have an aliphatic hydrocarbon group with 1 to 8 carbon atoms in its main chain, and $R_3$ represents a hydrogen atom or alkyl group with 1 to 6 carbon atoms.

2. A polynuclear polyphenol expressed by General Formula (2) below:

General Formula (2)

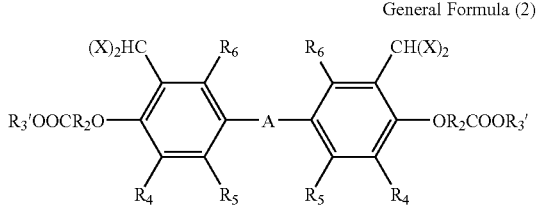

wherein A represents a saturated aliphatic hydrocarbon group with 1 to 9 carbon atoms, $R_2$ represents a single-ring or condensed-ring aromatic hydrocarbon group with 6 to 15 carbon atoms that may have an aliphatic hydrocarbon group with 1 to 8 carbon atoms in its main chain, $R_4$, $R_5$ and $R_6$ each independently represent a hydrogen atom, alkyl group with 1 to 8 carbon atoms or alkoxy group with 1 to 8 carbon atoms, $R_3'$ represents a hydrogen atom or primary or secondary alkyl group with 1 to 6 carbon atoms, and X represents a hydroxyphenyl group expressed by General Formula (3) below:

General Formula (3)

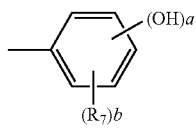

wherein R₇ represents a hydrogen atom, alkyl group with 1 to 8 carbon atoms or alkoxy group with 1 to 8 carbon atoms, a represents an integer of 1 to 3, and b represents an integer of 0 to 4, with a proviso that 1≦a+b≦5 wherein if b is 2 or greater, each R₇ may be the same or different.

3. A polynuclear phenol according to claim 2, wherein General Formula (3) above is expressed by General Formula (4) below:

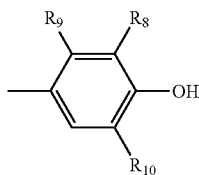

General Formula (4)

wherein R₈, R₉ and R₁₀ are each independently the same as R₇ defined in General Formula (3).

4. A bis(formylphenyl)alkane according to claim 1, which is selected from the group consisting of:
bis(3-formyl-4-(4-methoxycarbonylphenyl)methoxyphenyl)methane,
bis(3-formyl-5-methyl-4-(2-(4-methoxycarbonylphenyl)ethyl)oxyphenyl)methane
bis(3-formyl-4-(3-methoxycarbonylphenyl)methoxyphenyl)methane,
bis(3-formyl-4-(4-methoxycarbonylphenyl)oxyphenyl)methane,
2,2-bis{3-formyl-4-(4-methoxycarbonylphenyl)methoxyphenyl}propane,
bis[2-(4-methoxycarbonylphenyl)methoxy-3-formyl-5-methylphenyl]methane,
bis{3-formyl-4-(2-methoxycarbonylphenyl)oxyphenyl}methane,
bis[3-formyl-4-[2-{4-(2-methoxycarbonylethyl)phenyl}ethyl]oxyphenyl]methane,
bis[3-formyl-4-(2-{4-(methoxycarbonylmethyl)phenyl}ethyl)oxyphenyl]methane,
bis(3-formyl-4-(5-methoxycarbonyl-1-naphthyl)methoxyphenyl)methane,
1,2-bis(3-formyl-4-(4-methoxycarbonylphenyl)methoxyphenyl)ethane,
bis(3-formyl-4-(4-carboxyphenyl)methoxyphenyl)methane, and
2,2-bis{3-formyl-4-(4-carboxyphenyl)methoxyphenyl}propane.

5. A polynuclear polyphenol according to claim 2, which is selected from the group consisting of:
bis(3-bis(2,5-dimethyl-4-hydroxyphenyl)methyl-4-(4-carboxyphenyl)methoxyphenyl)methane,
bis(3-bis(3-methyl-4-hydroxyphenyl)methyl-4-(4-carboxyphenyl)methoxyphenyl)methane,
bis(3-bis(2,3,5-trimethyl-4-hydroxyphenyl)methyl-4-(4-carboxyphenyl)methoxyphenyl)methane,
bis(3-bis(2-methyl-5-cyclohexyl-4-hydroxyphenyl)methyl-4-(4-carboxyphenyl)methoxyphenyl)methane,
2,2-bis(3-bis(2,5-dimethyl-4-hydroxyphenyl)methyl-4-(4-carboxyphenyl)methoxyphenyl)propane,
2,2-bis(3-bis(2,5-dimethyl-4-hydroxyphenyl)methyl-4-(4-carboxyphenyl)methoxy-5-methylphenyl)propane,
1,2-bis(3-bis(2,5-dimethyl-4-hydroxyphenyl)methyl-4-(4-carboxyphenyl)methoxyphenyl)ethane,
bis(3-bis(5-methyl-2-hydroxyphenyl)methyl-4-(4-carboxyphenyl)methoxyphenyl)methane,
bis(3-bis(4,6-dimethyl-2-hydroxyphenyl)methyl-4-(4-carboxyphenyl)methoxyphenyl)methane,
bis(3-bis(2-methyl-4,5-dihydroxyphenyl)methyl-4-(4-carboxyphenyl)methoxyphenyl)methane, and
bis(3-bis(2,3,4-trihydroxyphenyl)methyl-4-(4-carboxyphenyl)methoxyphenyl)methane.

* * * * *